United States Patent
Schuit et al.

(10) Patent No.: US 11,991,965 B2
(45) Date of Patent: May 28, 2024

(54) **POTATO LATE BLIGHT RESISTANCE IN POTATO, *SOLANUM TUBEROSUM* L**

(71) Applicant: Bejo Zaden B.V., Warmenhuizen (NL)

(72) Inventors: Cornelis Anthonius Schuit, Warmenhuizen (NL); Martinus Jacobus Theodorus Klaver, Warmenhuizen (NL); Marie Anne Sophie Jeanne Elisabeth Hardy, Warmenhuizen (NL); Dora Lisa Moita E Coelho, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 341 days.

(21) Appl. No.: 17/293,204

(22) PCT Filed: Nov. 11, 2019

(86) PCT No.: PCT/EP2019/080885
§ 371 (c)(1),
(2) Date: May 12, 2021

(87) PCT Pub. No.: WO2020/099330
PCT Pub. Date: May 22, 2020

(65) Prior Publication Data
US 2022/0000052 A1    Jan. 6, 2022

(30) Foreign Application Priority Data
Nov. 13, 2018    (NL) .................. 2021988

(51) Int. Cl.
*A01H 6/82* (2018.01)
*A01H 1/00* (2006.01)

(52) U.S. Cl.
CPC ......... *A01H 1/1245* (2021.01); *A01H 6/827* (2018.05)

(58) Field of Classification Search
None
See application file for complete search history.

(56) References Cited

U.S. PATENT DOCUMENTS

2008/0172757 A1* 7/2008 Blatter ............... A01H 6/827
                                                    800/265
2019/0269095 A1    9/2019 Klaver et al.

FOREIGN PATENT DOCUMENTS

WO    2006111388 A1    10/2006
WO    2018019359 A1    2/2018

OTHER PUBLICATIONS

Bormann et al. 2004. MPMI vol. 17, No. 10, pp. 1126-1138. Publication No. M-2004-0727-01R.*
Tian wt al. 2008. Can. J. Plant Sci. 88: 599-610.*
Li et al. 2012. Theor Appl Genet 124:1339-1350.*
Danan et al. BMC Plant Biology 2011, 11:16.*
Adly et al. 2023. Plants 2023, 12, 232. https://doi.org/10.3390/plants12020232.*
Bormann et al., "Tagging Quantitative Trait Loci for Maturity-Corrected Late Blight Resistance in Tetraploid Potato with PCR-Based Candidate Gene Markers," 2004, Molecular Plant-Microbe Interactions, vol. 17, Issue 10, pp. 1126-1138.
Cooke et al., "Genome Analyses of an Aggressive and Invasive Lineage of the Irish Potato Famine Pathogen," 2012, PLoS Pathog., vol. 8, No. 10, p. e1002940.
Danan et al., "Construction of a potato consensus map and QTL meta-analysis offer new insights into the genetic architecture of late blight resistance and plant maturity traits," 2011, BMC Plant Biology, vol. 11, Issue 16, pp. 1-16.
Leonards-Schippers et al., "Quantitative Resistance to Phytophthora infestans in Potato: A Case Study for QTL Mapping in an Allogamous Plant Species," 1994, Genetics, vol. 137, pp. 67-77.
Li et al., "Conditional QTL underlying resistance to late blight in a diploid potato population," 2012, Theor Appl Genet., vol. 124, pp. 1339-1350.
Meijer et al., "*Solanum tuberosum* L.; Sevilla; vos2006-001-001," 2017, Community Plant Variety Office, application No. A201702287.

\* cited by examiner

*Primary Examiner* — Medina A Ibrahim
(74) *Attorney, Agent, or Firm* — The Webb Law Firm

(57) ABSTRACT

Provided herein is a genetic determinant for potato late blight resistance caused by the plant pathogen Phytophtora infestans, in potato, *Solanum tuberosum* L. Specifically, disclosed herein are *Solanum tuberosum* plants having a genetic determinant providing qualitative resistance against Phytophtora infestans which genetic determinant is located in the distal part of chromosome 12 of *Solanum tuberosum* between positions 60.1 and 67.2. Mbp and which genetic determinant is obtainable from a *Solanum tuberosum* plant with deposit No. NCIMB 43225.

8 Claims, 3 Drawing Sheets

POTATO LATE BLIGHT RESISTANCE IN POTATO, *SOLANUM TUBEROSUM* L

CROSS-REFERENCE TO RELATED APPLICATIONS

This application is the United States national phase of International Application No. PCT/EP2019/080885 filed Nov. 11, 2019, and claims priority to Netherlands Patent Application No. 2021988 filed Nov. 13, 2018, the disclosures of which are hereby incorporated by reference in their entirety.

BACKGROUND

Description

The present invention relates to a novel genetic determinant for potato late blight resistance caused by the plant pathogen *Phytophthora infestans*, in potato, *Solanum tuberosum* L.

Potato, or *Solanum tuberosum* L., is a widely grown crop, accounting for a global harvest which was almost 380 million metric tonnes in 2016, grown on about 20 million hectares. With this yield, potato is a major food crop. Cultivation of potato starts with selected tubers from crosses which are vegetatively propagated in several successive rounds since *Solanum tuberosum* is a tetraploid crop where propagation by seed is difficult because of the high level of genetic variation in offspring. However, developing botanical seeds of tetraploid potato hybrids which are genetically sufficiently stable to serve as propagation material was recently reported (WO2018/019359).

Next to breeding at the tetraploid level, also breeding with potato on the diploid level is performed. The latter has as one of the advantages that with fewer generations of backcrossing a good level of homozygosity can be attained.

Potato is affected by many pests and diseases which are easily contracted since the crop is annually propagated by growing new tubers from selected basis material. However, a stringent control mechanism is in place, thereby considerably reducing the risk of disease outbreaks.

The most critical disease which affects potato is potato late blight, caused by the oomycete *Phytophthora infestans*. *Phytophthora infestans* is well known since it was the causal agent of the Great Famine in Ireland round 1840-1847 which caused the death of a million people because of starvation and also led to another million people emigrating from Ireland. Despite many efforts to breed for resistance and strict protocols aiming at reducing the spread of infected material, potato late blight remains the disease which causes most economical damage in the crop potato.

*Phytophthora infestans* can infect all tissues of the potato plant: leaf, stem, and tubers; infected tissues show typical black necrotic lesions. The optimal conditions for this pathogen are high humidity (more than 90%) combined with lower temperatures. *Phytophthora infestans* has a hemibiotrophic cycle, which means that it can propagate through both a sexual and an asexual cycle. The result of the asexual cycle is the production of sporangia and zoospores, while after mating with a strain of a different, heterothallic, type it produces oospores. Through the sexual cycle, *Phytophthora infestans* can quickly increase the genetic diversity of the population. This also makes it difficult to breed for resistance against potato late blight; if successes are recorded, these are often related to resistance against certain strains of potato late blight. Due to the described sexual cycle, where the genome is rearranged, *Phytophthora infestans* is able to circumvent plant immunity. In fact, the large genome of 240 Mb and the presence of many diverse transposons carrying different effectors, make its adaptation highly dynamic and therefore difficult to manage.

SUMMARY

Disclosed is the recognition and mapping of the genomic regions of the accession 20170089, involved in conferring resistance against *Phytophthora infestans*. For doing so, a BC1 mapping population was used, originating from the cross of the susceptible accession 20170088 with the resistant accession 20170089.

The other parental line used in this project was *Solanum* accession 20170088, which is a self-compatible inbred line, which is highly susceptible to *Phytophthora infestans*. Since it has a high level of inbreeding, it is homologous for many alleles, including the dominant self-incompatibility inhibitor Sli gene. It was chosen as a parent also because of its good pollen quality that resulted in successful crosses.

To study the genetic basis for the resistance, a BC1 mapping population was used for this project. The population originated from the cross of the diploid *Solanum* accession 20170089 with 20170088; another *Solanum* accession, susceptible for potato late blight. The BC1 population originating from the cross of the susceptible 20170088 with the resistant 20170089 was evaluated to identify genomic regions involved in resistance to potato late blight.

The main goal of the research was to identify genomic regions responsible for potato late blight resistance in the *Solanum* accession 20170089.

BRIEF DESCRIPTION OF THE DRAWINGS

Figures

FIG. 2 shows interval mapping for potato late blight resistance in the BC1 mapping population. The black dotted line represents the significance threshold (LOD=3). The LOD value (red line) indicates that the most likely position for a major QTL is mapped in the end of linkage group 12, with the maximum LOD score of 38.83.

DETAILED DESCRIPTION

Figure 1:
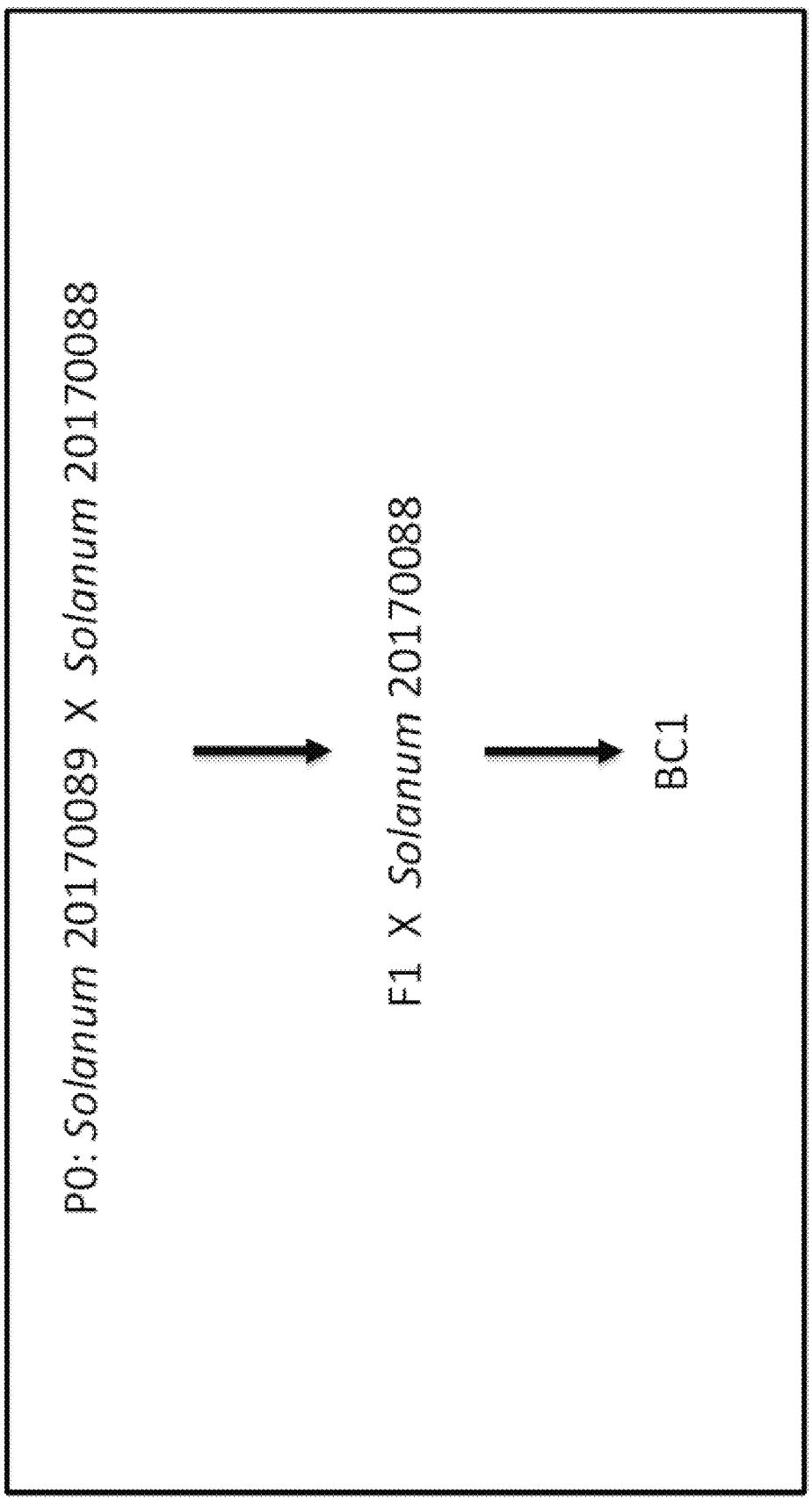
FIG. 1: Accession 20170089 was used as donor for the resistance, while susceptible accession 20170088 (male) was used for a.o. good pollen quality.

Seed lots are germinated on paper filter under continuous light at 15° C. Germination is established after 21-25 days. Once germination succeeded, the young plants were transplanted in 96-pots trays and placed in the greenhouse at room temperature. The 20170088 and 20170089 plants derived from material propagated in tissue culture were used as negative and positive controls respectively in the trial.

Inoculum preparation: the *Phytophthora infestans* isolate blue13 was used in this project (Cooke D. E. L., C. L., Raffaele S, Bain R A, Cooke L R, Etherington G J, Deahl K L, Farrer R A, Gilroy E M, Goss E M, Grunwald N J, Hein I, MacLean D, McNicol J W, Randall E, Oliva RF, Pel M A, Shaw D S, Squires J N, Taylor M C, Vleeshouwers V G A A, Birch P R J, Lees A K, (2012) Genome analyses of an aggressive and invasive lineage of the Irish potato famine pathogen. PLoS Pathog 8(10): e1002940). This isolate belongs to an A2 mating type and it is known for its high aggressiveness. The isolate was maintained and propagated on solid pea agar; before inoculation the pathogen was propagated every 2 weeks. The plates with sporulating mycelium were scraped with demi-water to harvest the sporangia. The concentration of the sporangia in the suspension adjusted to circa $4 \times 10^4$ sporangia/ml.

Potato late blight disease trial: for the disease trial, the BC1 mapping population, which consisted of 217 plants, was planted in the field in early summer together with 6 plants of each parental line and 6 F1 plants. Two rows of a susceptible tomato cultivar were interspaced between every two rows of potato plants to ensure a reliable inoculation. The inoculation was done in the late evening (around 8 PM), so the spores could benefit from the dew on the leaves and from the absence of direct sunlight. The inoculations were performed starting on week 5 after planting and repeated for three successive weeks when the weather conditions were suitable for the infection (preferably cool nights and high air humidity). The disease development was scored over time by visual assessment of the lesions on leaves and stems. Four weekly successive assessments were performed from the moment the first disease symptom was observed on the plant.

The score was determined on a scale from 0 to 9 (0 means that the plant is dead and 9 corresponds to no symptoms observed). The susceptible parent 20170088 and the resistant parent 20170089 were used as negative and positive control respectively.

DNA extraction and purification: DNA from individual plants was isolated using standard molecular techniques which are known to the person skilled in the art. The quality of the DNA was checked by electrophoresis in 1.5% agarose-TBE gel and its concentration was measured with a Nanodrop Microvolume Spectrophotometer.

Evaluation of the disease trial: the assessment was done at 4 different moments, with the aim to collect phenotypic data at different time points. The 4th assessment was the most reliable for a QTL analysis because of a higher standard deviation (St. Dev.=2.32), meaning that the observation were better covering the whole range of scores. Therefore the following data are referring to this assessment. In total 204 plants could be assessed, of these, 88 were completely susceptible to potato late blight, scoring from 0 to 4. Fifty individuals scored from 5 or 6, indicating a partial level of resistance. Eventually, 31 plants showed none or few symptoms, scoring from 7 to 9.

For genetic linkage mapping, the Illumina Infinium platform was used for genotyping the parental lines and the FL. Three-hundred-and-four informative SNP's, well distributed along the entire genome, were selected for genotyping the mapping population. The SNP markers selected were renamed based on the chromosome's number and position based on the potato reference genome. The SNP-markers were first converted into suitable KASP assays. Then, the assays were used for the KASP genotyping. Finally, the linkage analysis and the genetic map were carried out in JoinMap 4.1 The individuals that were used in the field test, were analysed as separated mapping populations. Of the original 304 SNP markers, 234 were informative and of good quality. In total, 227 markers were submitted for the construction of the linkage map in JoinMap 4.1.

QTL analysis: phenotypic data of the trial were collected at 4 different time points. All the observations at different time points were submitted to QTL analysis; however, those summarized in the following paragraphs referred to the 4th evaluation, which resulted to have the best distribution curve (data not shown). These data were combined with the genotypic data in MapQTL 6. Through the Interval Mapping analysis, one major QTL region was found in the long arm of chromosome 12, corresponding to the SNP marker 12_36. The LOD score for this marker was 25.68 at position 59,870,038 bp or 108 cM.

Figure 2:
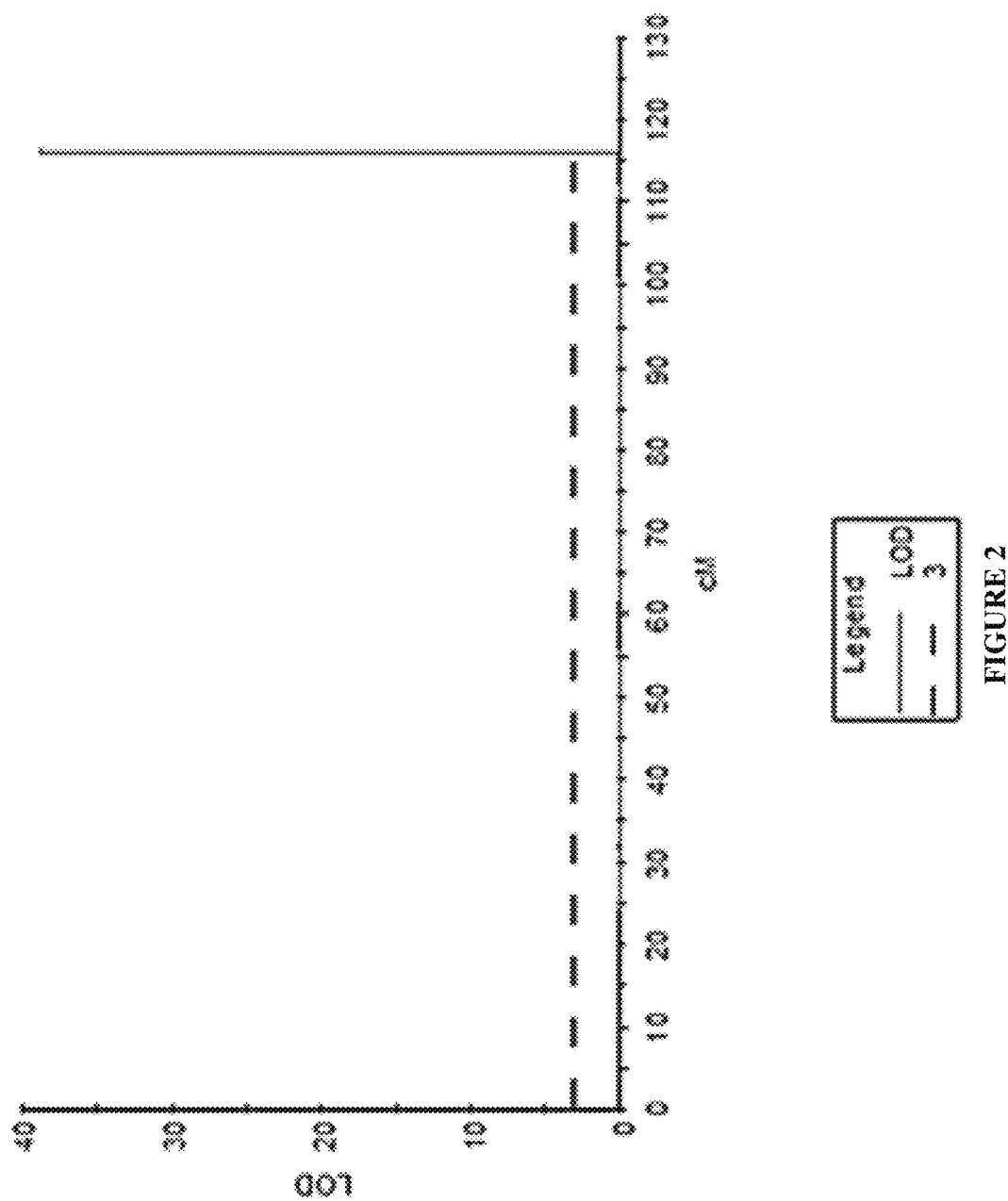
FIG. 2.

Fifteen new SNP markers were run to have a better coverage of the distal end of chromosome 12, where the most significant QTL was identified. Thus, a new linkage map of chromosome 12 was implemented in JoinMap 4.1 (FIG. 2) and then submitted to a QTL analysis in MapQTL 6. The KASP marker 44 was then selected as cofactor in MapQTL 6 for the Multiple QTL Mapping analysis. The major QTL, explaining 56.1% of the total variance was confirmed to be at the distal region of chromosome 12 within the physical interval of 61,766,882-67,153,289 bp. The large genetic effect linked to this QTL suggests that its presence is highly significant for conferring potato late blight resistance in this specific mapping population (LOD=38.83).

Figure 3:
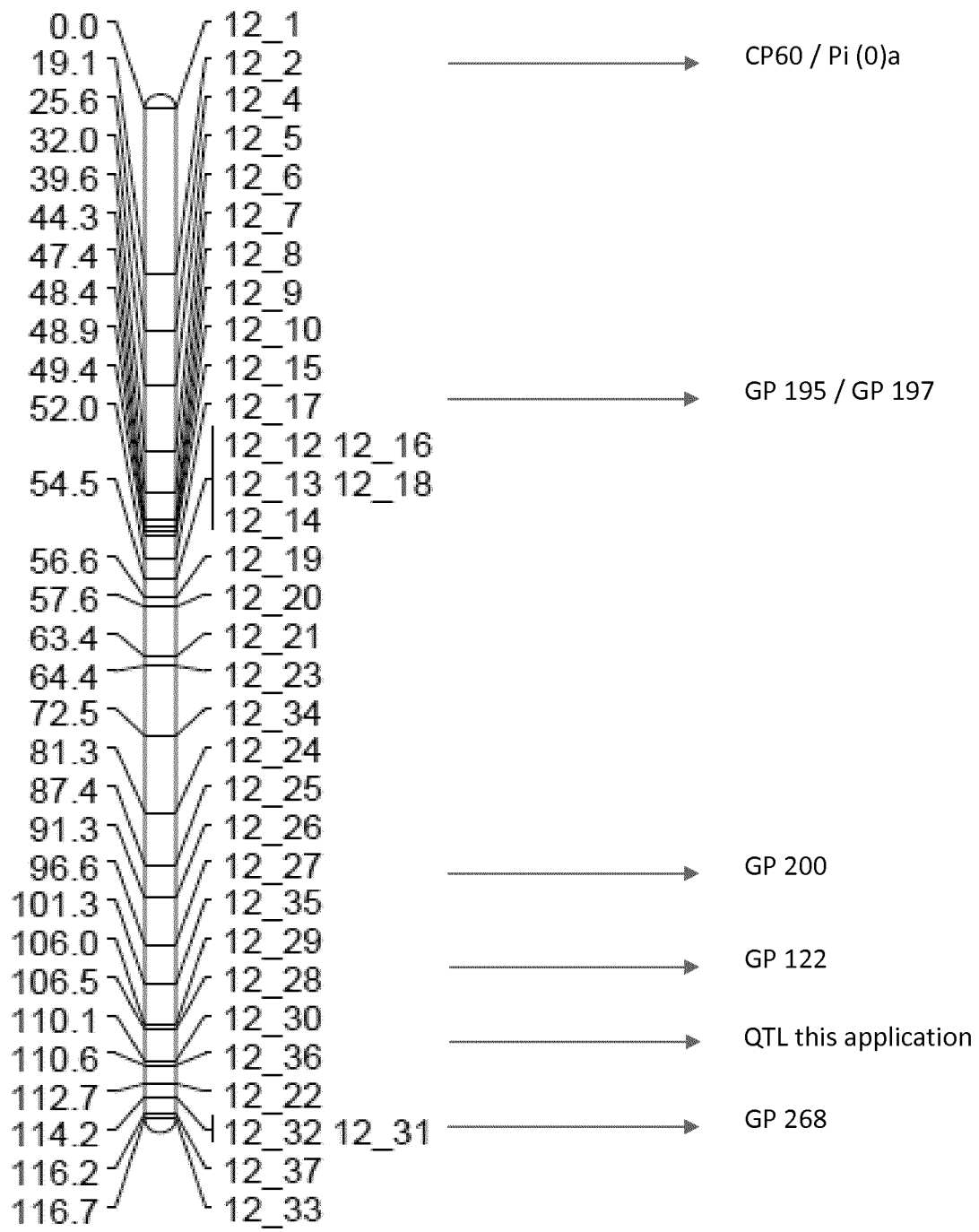
FIG. 3: Linkage group 12 of *Solanum tuberosum* with novel markers represented. Markers here are ordered on basis of genetic mapping, not on their physical location. Reference are made to the genetic markers determined by Leonards-Schippers et al. showing the inversion of the current map of chromosome 12 in relation to the genetic map presented by these authors.

Applicant is aware of a publication by Leonards-Schippers et al. (Leonards-Schippers, C. W. Gieffers, R. Schafer-Pregl, E. Ritter, S. J. Knapp, F. Salamini and C. Gebhardt (1994) Quantitative Resistance to *Phytophthora Infestans* in Potato: A Case Study for QTL Mapping in an Allogamous Plant Species. Genetics 137: 67-77.) where a QTL, linked to potato late blight, is described. However, with the now accepted representation of *S. tuberosum* chromosomes, this QTL is located at the opposite end (proximal) end of chromosome 12; see also FIG. 3.

The sequences belonging to these genes were extracted from the public domain and used to locate the genes from this publication on the genetic map developed by the applicant. Comparison of the chromosomal map in this publication with data obtained from this research learned that the map of chromosome 12 in the publication of Leonards-Schippers et al. is inverted in relation to the molecular map resulting from experimental data from the applicant. As is common practice, applicant represented these data with the short arm of the chromosome involved, at the top of the figure. The map position of the QTL described in this application is, in the representation of the applicant, around 1,6 Mbp at the proximal side of this chromosome whereas the QTL according to this invention is located in the distal region of chromosome 12 in the region between 60.1 and 67.2 Mbp.

This disclosure provides a novel major dominant QTL that has not been identified before in other breeding programs. Also in chromosome 3, there is no record of the detection of potato late blight resistant genes. The low explained variance for this QTL is indeed caused by a minor contribution of its effect. However, a better phenotypic variance explanation could be calculated by increasing the marker density that covers that genomic region.

Information relating to genetic resources: On Oct. 5, 2018 a deposit of the aforementioned BC1 generation was made at National Collection of Industrial Food and Marine Bacteria, NCIMB Ltd, Bucksburn, ABERDEEN Scotland, AB21 9YA United Kingdom, as accession NCIMB 43225.

ABBREVIATIONS

BC1 Back cross generation 1 is a first crossing of a hybrid with one of its parental lines F1 First generation of a cross between distinctly different parental types RH Relative humidity QTL A quantitative trait locus (QTL) is a locus which correlates with variation of a quantitative trait in the phenotype of a population of organisms

The invention claimed is:

1. A *Solanum tuberosum* plant comprising in its genome a genetic determinant providing qualitative resistance against *Phytophthora infestans*, wherein the genetic determinant is located in the distal part of chromosome 12 of said *Solanum tuberosum* between positions 60.1 and 67.2 Mbp and comprising a quantitative trait locus at 59,870,038 bp of chromosome 12, representative seed of said *Solanum tuberosum* plant deposited with NCIMB under Accession No. NCIMB 43225.

2. The *Solanum tuberosum* plant according to claim 1, wherein said *Solanum tuberosum* plant is grown from a seed.

3. The *Solanum tuberosum* plant according to claim 2, wherein said seed is diploid.

4. The *Solanum tuberosum* plant according to claim 2, wherein said seed is tetraploid.

5. A tuber or plant part of the *Solanum tuberosum* plant according to claim 1, wherein the tuber or plant part comprises the genetic determinant and the quantitative trait locus on chromosome 12.

6. A seed of the *Solanum tuberosum* plant according to claim 1, wherein the seed comprises the genetic determinant and the quantitative trait locus on chromosome 12.

7. A method for providing a *Solanum tuberosum* plant having qualitative resistance against *Phytophthora infestans*, the method comprising introgressing a genetic determinant providing qualitative resistance against *Phytophthora infestans* and a quantitative trait locus at 59,870,038 bp of chromosome 12 from the *Solanum tuberosum* plant deposited with NCIMB under Accession No. NCIMB 43225 into a susceptible *Solanum tuberosum* plant, thereby producing the *Solanum tuberosum* plant having qualitative resistance against *Phytophthora infestans*.

8. A *Solanum tuberosum* plant obtainable by vegetative propagation of the *Solanum tuberosum* plant according to claim 1, wherein said vegetatively propagated *Solanum tuberosum* comprises in its genome the genetic determinant located in the distal part of chromosome 12 between positions 60.1 and 67.2 Mbp and the quantitative trait locus at 59,870,038 bp of chromosome 12.

\* \* \* \* \*

UNITED STATES PATENT AND TRADEMARK OFFICE
CERTIFICATE OF CORRECTION

| | | |
|---|---|---|
| PATENT NO. | : 11,991,965 B2 | Page 1 of 1 |
| APPLICATION NO. | : 17/293204 | |
| DATED | : May 28, 2024 | |
| INVENTOR(S) | : Cornelis Anthonius Schuit et al. | |

It is certified that error appears in the above-identified patent and that said Letters Patent is hereby corrected as shown below:

On the Title Page

Column 1, Title, Line 2, delete "TUBEROSUM L" and insert -- TUBEROSUM L. --

Column 2, Other Publications, Line 3, delete "wt" and insert -- et --

Column 2, Abstract, Line 2, delete "Phytophtora" and insert -- Phytophthora --

Column 2, Abstract, Line 6, delete "Phytophtora" and insert -- Phytophthora --

Column 2, Abstract, Line 8, delete "67.2." and insert -- 67.2 --

In the Specification

Column 1, Line 2, delete "TUBEROSUM L" and insert -- TUBEROSUM L. --

Signed and Sealed this
Thirtieth Day of July, 2024

Katherine Kelly Vidal
*Director of the United States Patent and Trademark Office*